(12) United States Patent
Braido et al.

(10) Patent No.: US 10,456,256 B2
(45) Date of Patent: Oct. 29, 2019

(54) HEART VALVE REPAIR

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Thomas M. Benson, Minneapolis, MN (US); Theodore Paul Dale, Corcoran, MN (US); Andrea N. Para, Centennial, CO (US); Mark Krans, Hopkins, MN (US); Mathias Charles Glimsdale, St. Michael, MN (US)

(73) Assignee: St. Jude Medical, Cardiology Division, Inc, St. Paul, MN (US)

( * ) Notice: Subject to any disclaimer, the term of this patent is extended or adjusted under 35 U.S.C. 154(b) by 0 days.

(21) Appl. No.: 15/076,849

(22) Filed: Mar. 22, 2016

(65) Prior Publication Data

US 2016/0278920 A1 Sep. 29, 2016

Related U.S. Application Data

(60) Provisional application No. 62/136,731, filed on Mar. 23, 2015.

(51) Int. Cl.
*A61F 2/24* (2006.01)
*A61B 17/00* (2006.01)
*A61B 17/04* (2006.01)

(52) U.S. Cl.
CPC ............ *A61F 2/2445* (2013.01); *A61F 2/246* (2013.01); *A61F 2/2442* (2013.01); *A61F 2/2448* (2013.01); *A61F 2/2454* (2013.01); *A61F 2/2487* (2013.01); *A61B 2017/00243* (2013.01); *A61B 2017/00867* (2013.01); *A61B 2017/0417* (2013.01); *A61B 2017/0464* (2013.01); *A61B 2017/0496* (2013.01); *A61F 2210/0004* (2013.01); *A61F 2210/0033* (2013.01); *A61F 2210/0061* (2013.01);
(Continued)

(58) Field of Classification Search
None
See application file for complete search history.

(56) References Cited

U.S. PATENT DOCUMENTS 4,275,469 A 6/1981 Gabbay
4,491,986 A 1/1985 Gabbay
(Continued)

FOREIGN PATENT DOCUMENTS

DE 19857887 A1 7/2000
DE 10121210 A1 11/2002
(Continued)

OTHER PUBLICATIONS

Catheter-implanted prosthetic heart valves, Knudsen, L.L., et al., The International Journal of Artificial Organs, vol. 16.
(Continued)

*Primary Examiner* — Suba Ganesan
(74) *Attorney, Agent, or Firm* — Lerner, David, Littenberg, Krumholz & Mentlik, LLP

(57) ABSTRACT

A device for repairing a native heart valve includes a reinforcing structure configured to couple to a portion of the native heart valve to remodel a geometry of the native heart valve, and at least one supporting member connected to the reinforcing structure.

6 Claims, 9 Drawing Sheets

(52) U.S. Cl.
CPC .......... *A61F 2220/0016* (2013.01); *A61F 2230/0065* (2013.01); *A61F 2230/0095* (2013.01); *A61F 2250/0003* (2013.01); *A61F 2250/0018* (2013.01); *A61F 2250/0029* (2013.01)

(56) References Cited

U.S. PATENT DOCUMENTS

| | | | |
|---|---|---|---|
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,554,185 A * | 9/1996 | Block | A61F 2/2412 606/195 |
| 5,855,601 A | 1/1999 | Bessler et al. | |
| 5,935,163 A | 8/1999 | Gabbay | |
| 5,961,549 A | 10/1999 | Nguyen et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,869,444 B2 | 3/2005 | Gabbay | |
| 6,893,460 B2 | 5/2005 | Spenser et al. | |
| 6,908,481 B2 | 6/2005 | Cribier | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,524,331 B2 | 4/2009 | Birdsall | |
| RE40,816 E | 6/2009 | Taylor et al. | |
| 7,585,321 B2 | 9/2009 | Cribier | |
| 7,731,742 B2 | 6/2010 | Schlick et al. | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 2002/0036220 A1 | 3/2002 | Gabbay | |
| 2003/0023303 A1 | 1/2003 | Palmaz et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2005/0096726 A1 | 5/2005 | Sequin et al. | |
| 2005/0256566 A1 | 11/2005 | Gabbay | |
| 2006/0008497 A1 | 1/2006 | Gabbay | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0241748 A1 * | 10/2006 | Lee | A61F 2/2445 623/2.37 |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2011/0029072 A1 | 2/2011 | Gabbay | |
| 2012/0053680 A1 * | 3/2012 | Bolling | A61F 2/2445 623/2.11 |
| 2012/0123531 A1 * | 5/2012 | Tsukashima | A61F 2/2448 623/2.37 |
| 2012/0296419 A1 * | 11/2012 | Richardson | A61F 2/2445 623/2.36 |
| 2012/0303116 A1 | 11/2012 | Gorman, III et al. | |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584 06 A1 | 10/2005 |
| EP | 1598031 A2 | 11/2005 |
| FR | 2847800 A1 | 6/2004 |
| FR | 2850008 A1 | 7/2004 |
| WO | 91/17720 A1 | 11/1991 |
| WO | 97/16133 A1 | 5/1997 |
| WO | 98/32412 A2 | 7/1998 |
| WO | 99/13801 A1 | 3/1999 |
| WO | 01/028459 A1 | 4/2001 |
| WO | 01/49213 A2 | 7/2001 |
| WO | 01/054625 A1 | 8/2001 |
| WO | 01/056500 A2 | 8/2001 |

(56) References Cited

FOREIGN PATENT DOCUMENTS

| WO | 01/076510 A2 | 10/2001 |
| WO | 02/36048 A1 | 5/2002 |
| WO | 02/47575 A2 | 6/2002 |
| WO | 03/047468 A1 | 6/2003 |
| WO | 2005070343 A1 | 8/2005 |
| WO | 06/073626 A2 | 7/2006 |
| WO | 10/008548 A2 | 1/2010 |
| WO | 10/008549 A1 | 1/2010 |
| WO | 10/096176 A1 | 8/2010 |
| WO | 10/098857 A1 | 9/2010 |

OTHER PUBLICATIONS

Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
"Direct-Access Valve Replacement", Christoph H. Huber, et al., Journal of the American College of Cardiology, vol. 46, No. 2, (Jul. 19, 2005).
"Percutaneous Aortic Valve Implantation Retrograde From the Femoral Artery", John G. Webb et al., Circulation, 2006; 113:842-850 (Feb. 6, 2006).
"Minimally invasive cardiac surgery", M. J. Mack, Surgical Endoscopy, 2006, 20:S488-S492, DOI: 10.100/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Closed heart surgery: Back to the future", Samuel V. Lichtenstein, The Journal of Thoracic and Cardiovascular Surgery, vol. 131, No. 5, pp. 941-943.
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
U.S. Appl. No. 29/375,243, filed Sep. 20, 2010.

\* cited by examiner

HEART VALVE REPAIR

CROSS-REFERENCE TO RELATED APPLICATIONS

The present application claims the benefit of the filing date of U.S. Provisional Patent Application No. 62/136,731 filed Mar. 23, 2015, the disclosure of which is hereby incorporated herein by reference.

BACKGROUND OF THE INVENTION

The present disclosure relates to heart valve repair and, in particular, to structures for reinforcing heart valves. More particularly, the present disclosure relates to devices and methods for repairing the functionality of native valve leaflets.

Diseased and/or defective heart valves may lead to serious health complications. One method of addressing this condition is to replace a non-functioning heart valve with a prosthetic valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

In some instances, it may be undesirable to replace the native heart valve with a prosthetic device. Instead, devices and methods may be desirable to restore functionality to a non-functioning native valve.

SUMMARY OF THE INVENTION

In some embodiments, a device for repairing a native heart valve includes a reinforcing structure configured to couple to a portion of the native heart valve to remodel a geometry of the native heart valve, and at least one supporting member extending from the reinforcing structure and in contact with heart tissue.

In some embodiments, a device for repairing a native heart valve includes a tethering structure having a plurality of tethers, each of the plurality of tethers extending between a first end and a second end, the second end having an anchor for coupling to a portion of heart tissue to remodel a geometry of a native heart valve.

BRIEF DESCRIPTION OF THE DRAWINGS

Various embodiments of the present disclosure are disclosed herein with reference to the drawings, wherein.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

In conventional collapsible prosthetic heart valves, the stent is usually anchored within the native valve annulus via radial forces exerted by the expanding stent against the native valve annulus. Because such anchoring partly depends on the presence of calcification or plaque in the native valve annulus, it may be difficult to properly anchor the valve in locations where plaque is lacking (e.g., the mitral valve annulus). Additionally, in certain situations it may be preferable to restore native valve leaflet function instead of implanting a prosthetic device to replace that function.

In view of the foregoing, there is a need for further improvements to the devices, systems, and methods for restoring the function of a native heart valve, such as a mitral valve, a tricuspid valve, an aortic valve, or a pulmonary valve. Among other advantages, the present disclosure may address one or more of these needs. While many of the examples disclosed herein are described with reference to a specific valve (e.g., a mitral valve or a tricuspid valve), it will be understood that many of the examples are not so limited and that the concepts described apply equally to other heart valves unless expressly limited herein.

Blood flows through the mitral valve from the left atrium to the left ventricle. As used herein, the term "inflow," when used in connection with a mitral heart valve, refers to the end of the heart valve closest to the left atrium, whereas the term "outflow," when used in connection with a mitral heart valve, refers to the end of the heart valve closest to the left ventricle. When used in connection with an aortic valve, "inflow" refers to the end closest to the left ventricle and "outflow" refers to the end closest to the aorta. The same convention is applicable for other valves wherein "inflow" and "outflow" are defined by the direction of blood flow therethrough. When used in connection with apparatus for delivering the various repair devices described herein into a user, the terms "proximal," "distal," "leading" and "trailing" are to be taken as relative to a user using the disclosed delivery apparatus. "Proximal" or "trailing end" are to be understood as relatively close to the user and "distal" or "leading end" are to be understood as relatively farther away from the user. Also, as used herein, the words "substantially," "approximately," "generally" and "about" are intended to mean that slight variations from absolute are included within the scope of the structure or process recited.

Figure 1:
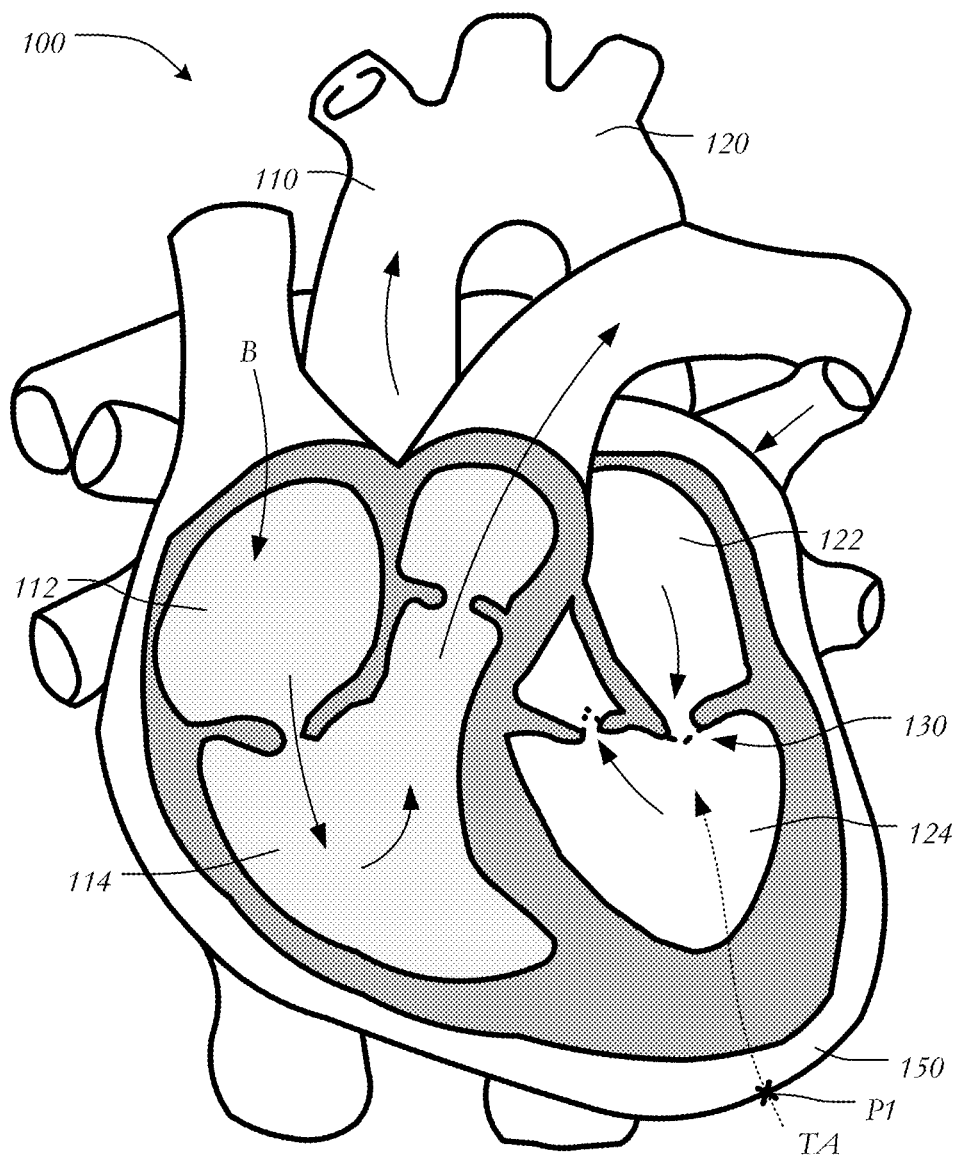
FIG. 1 is a schematic cutaway of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure in the left atrium as it fills with blood. As atrial pressure increases above that of the left ventricle, the mitral valve opens and blood passes toward the left ventricle. Blood flows through heart 100 in the direction shown by arrows "B".

A dashed arrow, labeled "TA", indicates a transapical approach for repairing or replacing heart valves, such as the mitral valve. In transapical delivery, a small incision is made between the ribs and into the apex of the left ventricle 124 at position "P1" in heart wall 150 to deliver a prosthesis or device to the target site.

Figure 2:
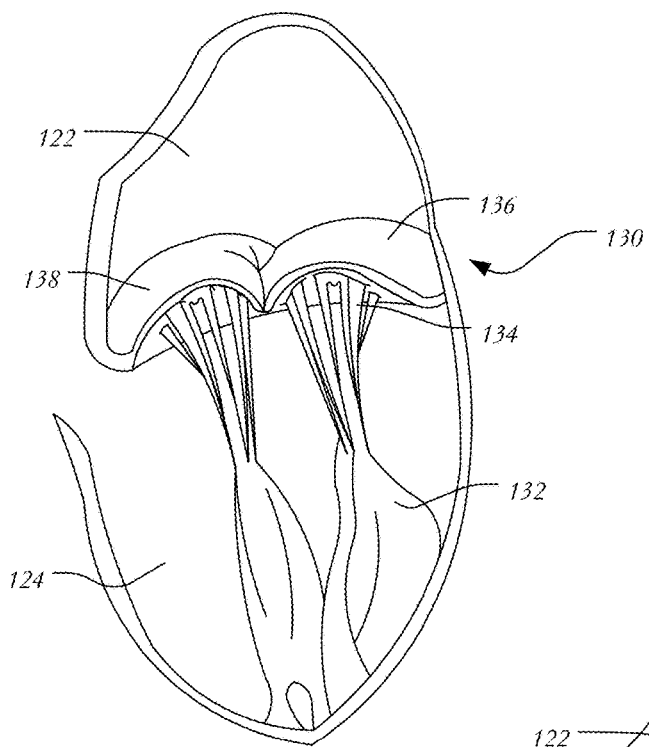
FIG. 2 is a schematic representation of a native mitral valve and associated structures during normal operation.

FIG. 2 is a more detailed schematic representation of native mitral valve 130 and its associated structures. Mitral valve 130 includes two flaps or leaflets, a posterior leaflet 136 and an anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing the backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

Figure 3:
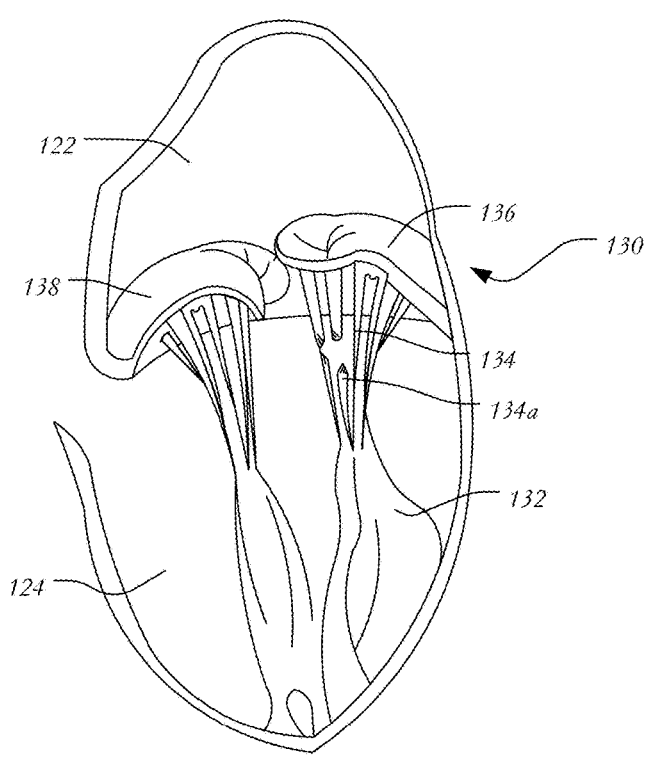
FIG. 3 is a schematic representation of a native mitral valve having a prolapsed leaflet.

FIG. 3 is a schematic representation of mitral valve prolapse as discussed above. Posterior leaflet 136 has prolapsed into left atrium 122. Moreover, certain chordae tendineae have stretched and others have ruptured. Because of damaged chordae 134a, even if posterior leaflet 136 returns to its intended position, it will eventually resume the prolapsed position due to being inadequately secured. Thus, mitral valve 130 is incapable of functioning properly and blood is allowed to return to the left atrium and the lungs. It will be understood that in addition to chordae damage, other abnormalities or failures may be responsible for mitral valve insufficiency.

Instead of completely replacing the native valve, however, structures may be implanted to improve and/or restore the function of the native valve by remodeling the geometry or perimeter of the native heart valve. The following structures may be used in conjunction with a native heart valve or in combination with prosthetic valves. Additionally, while the foregoing examples may describe certain concepts in connection with mitral valves, it will be appreciated that these concepts may be equally applicable to other heart valves.

Figure 4:
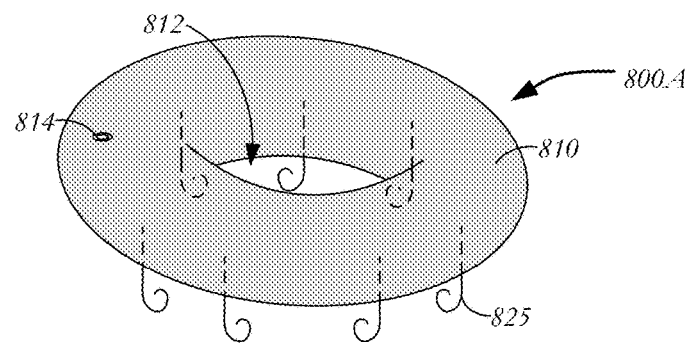
FIGS. 4 and 5 are schematic perspective views of toroidal reinforcing structures for supporting one or more portions of a native valve.

FIG. 4 illustrates reinforcing structure 800A for supporting one or more native mitral valve leaflets. Reinforcing structure 800A generally includes a collapsible and expandable toroidal body 810 defining an opening 812. Body 810 may be formed of nitinol, fabric, polymer or tissue-covered material that is shaped as a balloon-like structure. Body 810 may include inflation port 814 for receiving an inflation medium such as saline, a gas, a polymeric material, nitinol foam, a gel or the like to inflate the balloon from a collapsed condition to an expanded condition. Alternatively, body 810 may be formed of a shape-memory material (e.g., wire mesh) and configured to return to an expanded condition when released from a delivery device. Though a generic toroidal shape is shown, it will be appreciated that the shape of body 810 may be adjusted to match the native anatomy. For example, when being used to support a mitral valve, body 810 may be substantially saddle-shaped as will be described with reference to FIGS. 6-9. Body 810 may be disposed directly below the native mitral valve leaflets and progressively actuated (e.g., by gradual inflation when body 810 is a balloon-like structure) until proper coaptation of the native mitral valve leaflets is achieved. As shown, body 810 further includes a plurality of coils 825 extending from an underside thereof. Coils 825 may be flexible and capable of latching onto portions of heart tissue to fix body 810 at a predetermined location in a native valve annulus to support body 810. As body 810 is inflated, the geometry of the native heart valve may be remodeled and proper coaptation of the native leaflets may be accomplished. Body 810 may be located near the annulus of the mitral valve without interfering with the function and movement of the native heart leaflets. In some examples, body 810 may partially obstruct the opening between the native leaflets, but such obstructions may be minimal such that blood flow is not affected.

Figure 5:
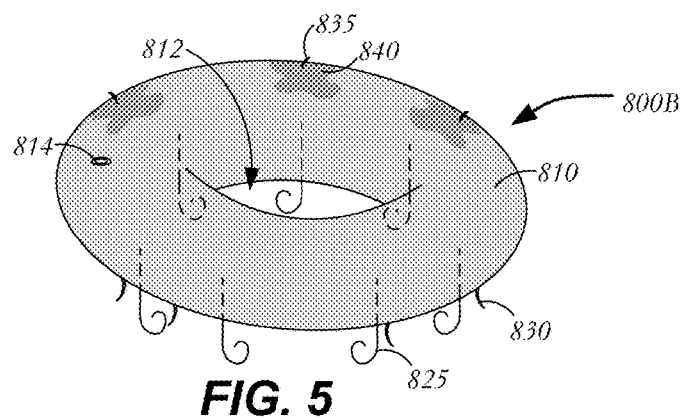

In a variation of reinforcing structure 800A, reinforcing structure 800B of FIG. 5 similarly includes body 810, opening 812, inflation port 814 and coils 825. Reinforcing structure 800B is configured to be implanted directly above the native valve leaflets and thus includes a plurality of hooks 830 arranged to latch onto the native leaflets. As body 810 is inflated, hooks 830 adjust the positions of the native leaflets and allow the native valve to function as intended. If additional stabilization of the body 810 is desired, prongs 835 may be used to couple body 810 to surrounding heart tissue. Designated portions 840 of body 810 may include prongs 835 adhered to their surface without puncturing the body so that the inflation media is retained therein. Thus, both prongs 835 and coils 825 may stabilize body 810 while hooks 830 allow for the adjustment of the position of the native valve leaflets. Reinforcing structures 800A,800B may be used in combination with prosthetic valves such that anchoring features on a stent may couple with body 810 to keep the prosthetic valve in the optimum position. For example, the shape of the anchoring features on the stent may be complementary to the shape of body 810.

Figure 6:
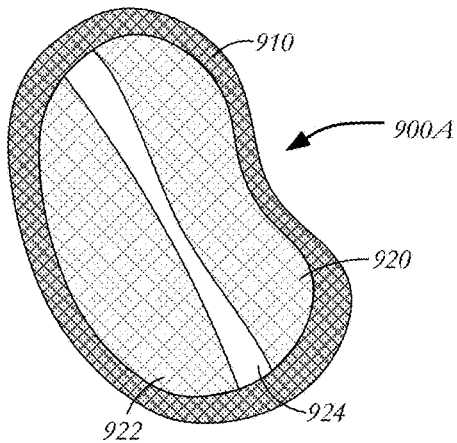
FIGS. 6-9 are schematic top views of reinforcing structures having flaps for supporting one or more portions of a native valve.

Instead of a balloon-like structure, reinforcements may be employed to ensure adequate coaptation of the native valve leaflets and prevent at least one of the leaflets from prolapsing. As shown in FIG. 6, reinforcing structure 900A includes a body 910 and flaps 920,922 defining a gap 924 therebetween. Body 910 is substantially saddle-shaped and configured to track the shape of the native valve being repaired (e.g., native mitral valve). It will be appreciated that a differently-shaped body may be employed depending on the patient and the valve to be restored. For example, an oval or D-shaped body may be used when restoring the function of a tricuspid valve. Attached to body 910 are two flaps 920,922 for adjusting the position of, or providing a backstop, mount or support to, the native anterior leaflet and the native posterior leaflet, respectively. Body 910 may be substantially rigid while flaps 920,922 may be more flexible than body 910 to support the native leaflets while allowing their movement. Body 910 and/or flaps 920,922 may be formed of nitinol, a fabric, a polymer (e.g., silicone, polytetrafluoroethylene, ultra-high molecular weight polyethylene), a metal (e.g., spring steel), tissue, nitinol-fabric hybrids or suitable combinations thereof. In one example, flaps 920,922 may be bioresorbable and configured to gradually provide less support over time.

Reinforcing structure 900A may be implanted surgically (e.g., transapically) underneath the native valve so that each flap supports a native valve leaflet. Alternatively, reinforcing structure 900A may be disposed above the native valve and include prongs (such as prongs 835 described above), hooks, clips or other attachment means on either body 910, leaflets 920,922, or both, for coupling to and supporting the native valve leaflets. Additionally, body 910 may include an adhesive or may be sewn to native valve tissue.

Figure 7:
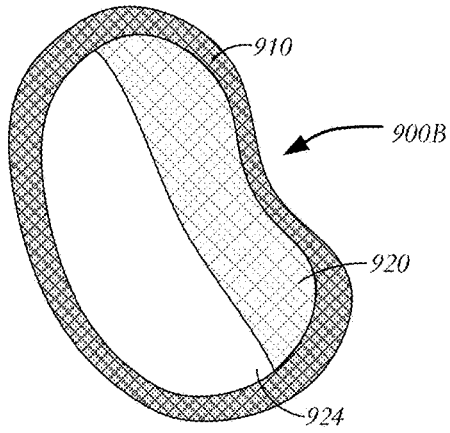
Figure 8:
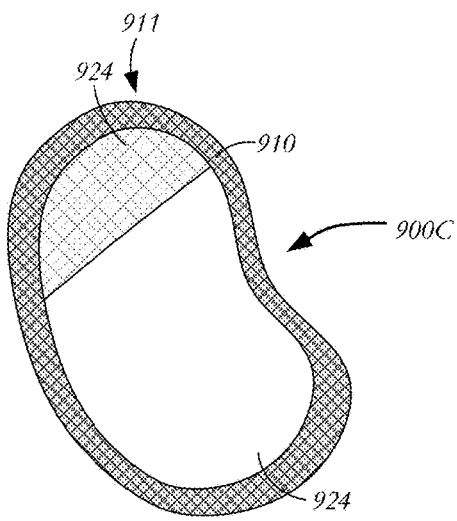
Figure 9:
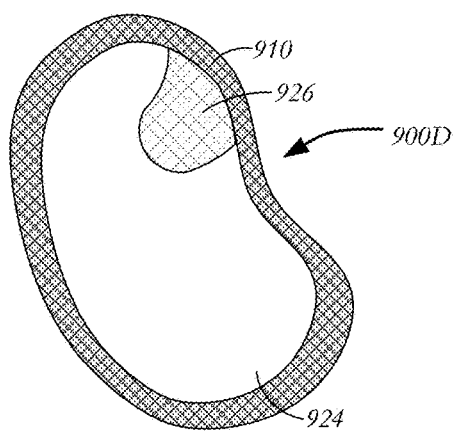

Reinforcing structure 900B, illustrated in FIG. 7, is a structure similar to structure 900A but includes a single flap 920 for supporting the anterior native leaflet if it is found that support for the posterior native leaflet is unnecessary. In another variation, shown in FIG. 8, reinforcing structure 900C includes body 910 and a flap 924 disposed at a short end 911 of body 910 and configured to support a portion of the native anterior commissure. In another variation, shown in FIG. 9, reinforcing structure 900D includes body 910 and a flap 926 disposed along an edge of body 910 and configured to support only a portion of the native anterior leaflet. It will be appreciated that a body and one or more flaps of selected shapes and sizes may used to support any portion of the native mitral valve, or other heart valve.

Figure 10A:
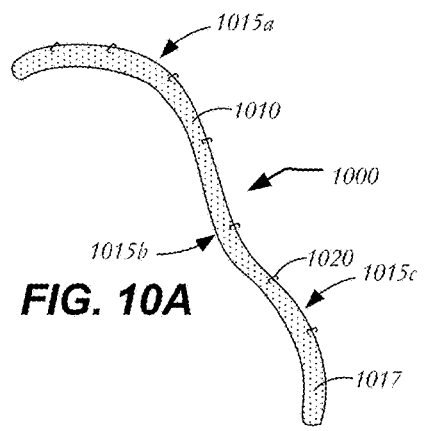
FIG. 10A is a schematic top view of a brace for supporting one or more portions of a native mitral valve.

In addition to modifying the movement of a leaflet by way of a backstop or an inflatable reinforcing structure, structures may be added to a native valve environment to remodel or modify the shape of a native valve. FIGS. 10A-D illustrate one such example of a perimeter modification structure in the form of perimeter brace 1000, and its use to modify the shape of the mitral valve 130. Perimeter brace 1000 generally is a rigid or semi-rigid body 1010 having a series of curvatures 1015*a-c* contoured to substantially match the perimeter of a healthy native valve (e.g., a fibrous ring of a mitral valve). Body 1010 may be formed of a suitable metal such as nitinol or stainless steel, a reinforced fabric, a polymer (e.g., silicone, polytetrafluoroethylene, ultra-high molecular weight polyethylene), tissue, nitinol-fabric hybrids or suitable combinations thereof. Body 1010 may also include a shape-memory material such as an electrically excitable shape-memory nitinol. Body 1010 may be hollow and capable of receiving a hydrophilic or hydrophobic material 1017 to change its shape as the material inflates the body. As shown, body 1010 has a predetermined shape that corresponds to the shape of approximately one-third of the perimeter of a mitral valve. It will be understood, however, that body 1010 may form a structure that spans the full perimeter of a native heart valve, or a portion of the native valve perimeter that is more or less than one-third. In some examples, certain curvatures, such as curvature 1015*b* of body 1010, may be slightly more pronounced than in the native valve so as to remodel the perimeter of the native valve when attached thereto. As shown in FIG. 10A, the attachment of body 1010 to the perimeter of the native valve annulus may be made by way of staples 1020. Alternatively, sutures, a biocompatible adhesive, or any other suitable method may be used.

Figure 10C:
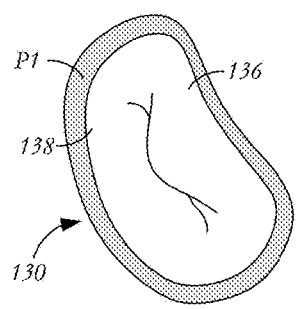
FIGS. 10C and 10D are schematic representations showing the effect of the brace of FIG. 10A on a native mitral valve.
Figure 10D:
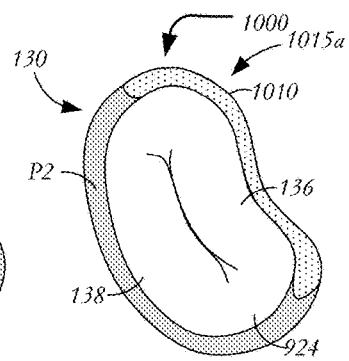
Figure 10B:
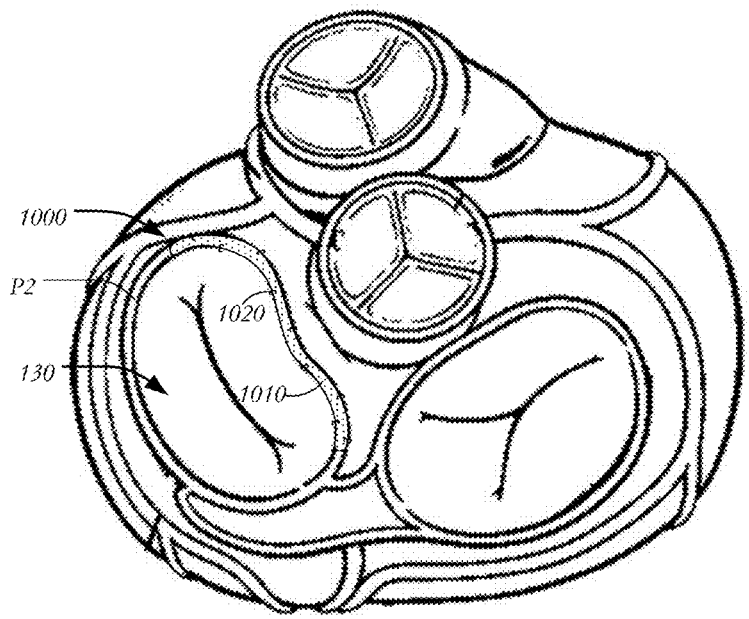
FIG. 10B is a schematic representation showing the use of the brace of FIG. 10A in a native mitral valve.

FIG. 10B illustrates the use of a brace 1000 on the fibrous ring perimeter P2 of native mitral valve 130. To better appreciate the effect of brace 1000, reference is made to FIGS. 10C and 10D. In FIG. 10C, mitral valve 130 having perimeter P1 includes posterior native leaflet 136 and anterior native leaflet 138 that do not properly coapt. Specifically, anterior native leaflet 138 has fallen below posterior native leaflet 136. By using brace 1000 as shown in FIG. 10D, body 1010 and specifically pronounced curvature 1015*a* remodels the perimeter of mitral valve 130 to perimeter P2. By changing the geometry of the native valve, the movement and positioning of posterior native leaflet 136 and anterior native leaflet 138 are changed such that the two leaflets properly coapt.

Figure 11A:
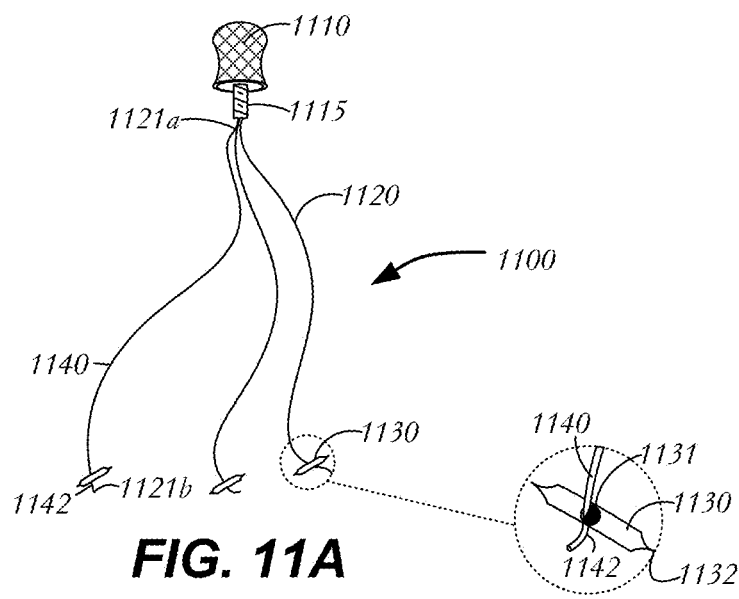
FIGS. 11A and 11B are, respectively, a perspective view of a first tethering device, and a schematic representation showing the use of the first tethering device on a native tricuspid valve.
Figure 11B:
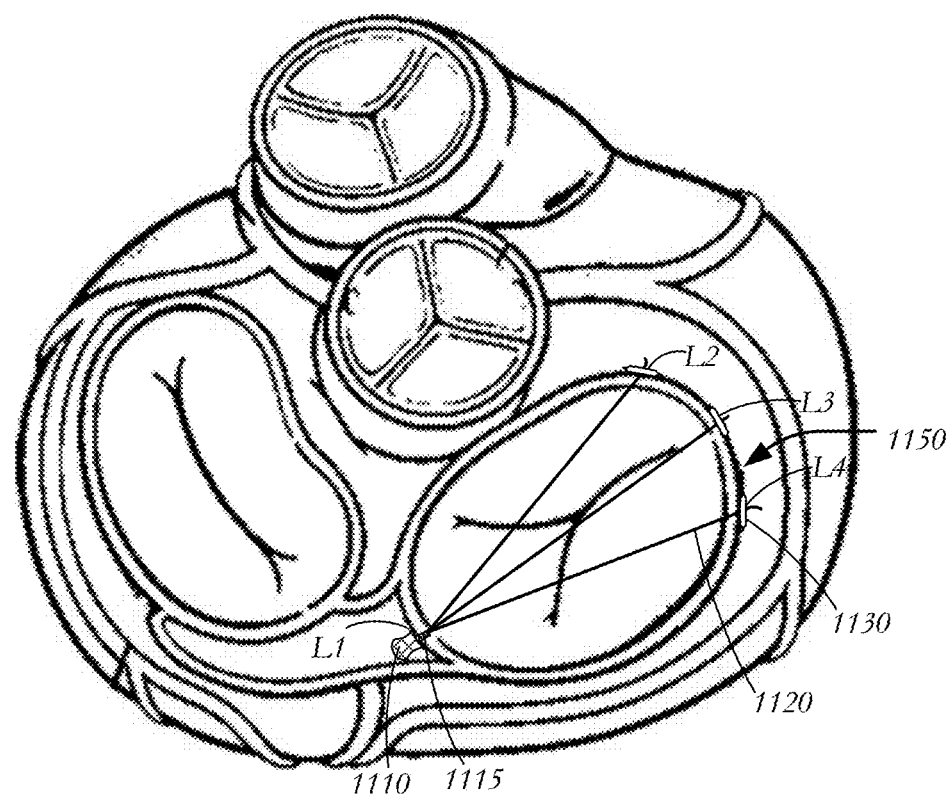

FIGS. 11A-B illustrate another example of a perimeter modification structure in the form of tethering device 1100. Tethering device 1100 generally includes core 1110, adjusting member 1115, tethers 1120 and anchors 1130. Although tethering device 1100 is shown as having three tethers 1120, the tethering device could include only one tether, or any number of tethers greater than one.

Adjusting member 1115 may be coupled to core 1110, and a plurality of tethers 1120 may be connected at first ends 1121*a* to the adjusting member and may have anchors 1130 near their second or free ends 1121*b*. Core 1110 may be formed of a suitable biocompatible material, including a metal such as stainless steel or nitinol, a reinforced fabric, a polymer (e.g., silicone, polytetrafluoroethylene, ultra-high molecular weight polyethylene), tissue, metal-fabric hybrids or suitable combinations thereof, and may be sized and configured for implantation in the heart, such as at the site of the left atrial appendage. Each tether 1120 may be formed of nitinol, stainless steel, GORE-TEX® or other suitable biocompatible filamentary material, and may generally include a functional portion 1140 between core 1110 and anchor 1130 and a terminal portion 1142 between anchor 1130 and second end 1121*b*. Each anchor 1130 may include a one-way gate 1131 that allows a tether 1120 to slide in a first direction through the anchor, but that restrains the tether from sliding through the anchor in the opposite direction. Coarse adjustment of the functional portion 1140 of each tether may be accomplished with one-way gate 1131. Fine adjustment of the lengths of functional portions 1140 may be made by rotating core 1110 relative to adjusting member 1115 to simultaneously shorten the tethers and change the geometry of the heart tissue. In some alternative examples, rotating core 1110 and adjusting member 1115 may be simply rotated in unison that tether 1120 wraps around the adjusting member like a spool and change the length of the tether. Alternatively, tethers 1120 may be pulled with a ratcheting mechanism or one-way gripping member through core 1110 to adjust the length of the tether.

The use of tethering device 1100 is shown in conjunction with tricuspid valve 1150 (FIG. 11B). As shown, core 1110 is coupled near a first end of heart valve 1150—in this case adjacent the left atrial appendage at location L1, and tethers 1120 extend across tricuspid valve 1150 to positions L2-L4. A piercing member 1132 on at least one end of each anchor 1130 may pierce through heart tissue at locations L2-L4 to fix the anchors, and thus the ends 1121*b* of tethers 1120, at those positions. Coarse adjustment of the length of the functional portion of each tether 1120 may be made by pulling the tether through the gate 1131 of its anchor 1130 to adjust the length of its terminal portion 1142. Thus, tethering device 1100 may remodel the shape of the tricuspid valve.

Figure 12A:
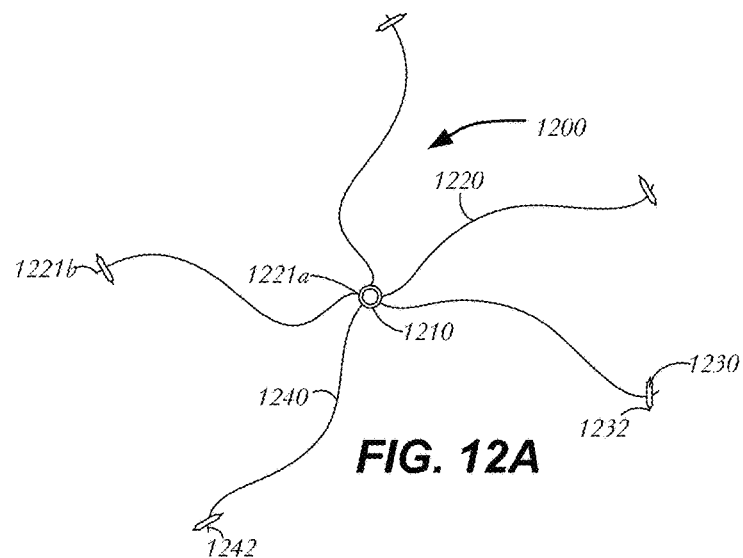
FIGS. 12A and 12B are, respectively, a top view of a second tethering device, and a schematic representation showing the use of the second tethering device on a native heart valve.

In another variation shown in FIG. 12A, tethering device 1200 includes a plurality of tethers 1220 coupled at their first ends 1221*a* to a hub 1210, and extending to second or free ends 1221*b*. The second end 1221*b* of each tether 1220 may include an anchor 1230 having at least one piercing member 1232. Hub 1210 and tethers 1220 may be formed of materials similar to those forming core 1110 and tethers 1120, respectively. In the example shown, tethering device 1200 does not include an adjusting member and the lengths of the functional portion 1240 and terminal portion 1242 of each tether 1220 may be adjusted by other means described below. Although tethering device 1200 is shown as having five tethers 1220, the tethering device could have only a single tether or any number of tethers greater than one.

Figure 12B:
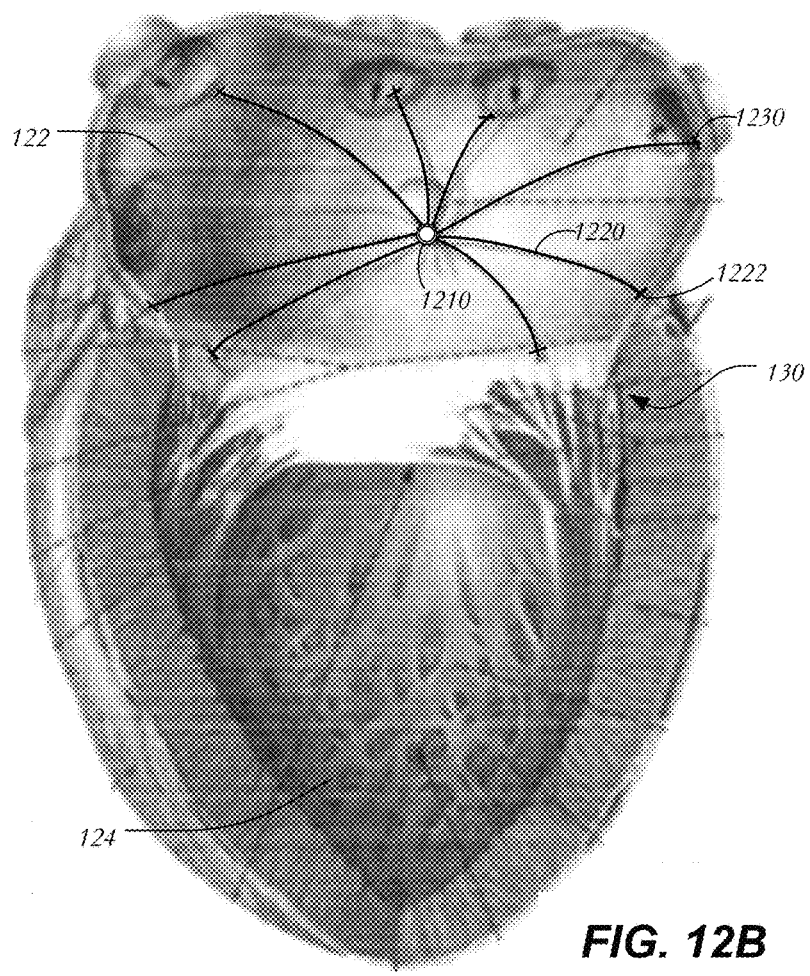

The use of tethering device 1200 is shown in conjunction with mitral valve 130 (FIG. 12B). As shown, hub 1210 is disposed in left atrium 122 and tethers 1220 extend across the left atrium to certain structures of the heart and are coupled thereto via anchors 1230. The lengths of functional portions 1240 of tethers 1220 may be adjusted in several ways. One way is to draw the tethers through anchors 1230 before, during or after implantation. In this technique, each anchor 1230 may be provided with a one-way gate such as gate 1131, a ratchet mechanism (not shown) or other structure enabling tether 1220 to be freely pulled through the anchor in one direction, but not in the other direction. Each tether 1220 may be drawn through its respective anchor 1230 until a desired reshaping of the left atrium 122 and mitral valve 130 has been achieved. Anchors 1230 will then hold tethers 1220 at these adjusted lengths. Another way to adjust the lengths of the functional portions 1240 of tethers 1220 is through electrical excitation (e.g., via a direct current) of a shape-memory material, such as nitinol, forming the tethers. In some examples, for example, a probe may be used to form a closed circuit with the tether and apply direct current to return the tether to a pre-set shape. The probe may also be in the form of an inductive charger so that no contact is required to change the length or shape of the tether.

Tethers 1220 may extend and couple to any combination of the following heart tissues: an atrial wall, a ventricular wall, one or more of a native valve leaflet, a fibrous ring, a papillary muscle, chordae tendineae, left atrial appendage, veins, arteries, etc. With tethering device 1200 in place and by adjusting the functional lengths of the tethers, the shape of the mitral valve 130 may be remodeled to allow proper coaptation of the native valve leaflets.

Figure 13A:
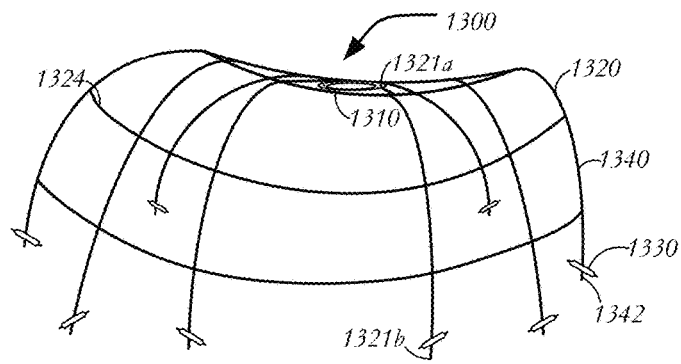
FIGS. 13A and 13B are, respectively, a perspective view of a third tethering device, and a schematic representation showing the use of the third tethering device on a native valve.

A dome tethering device 1300 may also be used to remodel heart tissue to aid leaflet coaptation. Referring to FIG. 13A, tethering device 1300 includes hub 1310 and a plurality of cascading tethers 1320 coupled at their first ends 1321*a* to hub 1310 and extending to second or free ends 1321*b*. The second end 1321*b* of each cascading tether 1320 includes an anchor 1330 having at least one piercing member. The lengths of the functional portion 1340 and the terminal portion 1342 of each cascading tether 1320 may be adjusted as necessary as described above (e.g., by pulling the tether a desired amount through a one-way gate in an anchor). Tethering device 1300 may further include one or more lateral tethers 1324 interconnecting cascading tethers 1320, the lateral tethers being configured to space the cascading tethers by a predetermined distance to form a net-like structure of tethers. While tethering device 1300 is shown as having eight cascading tethers 1320, the tethering device could have two cascading tethers or any number of cascading tethers greater than two.

Figure 13B:
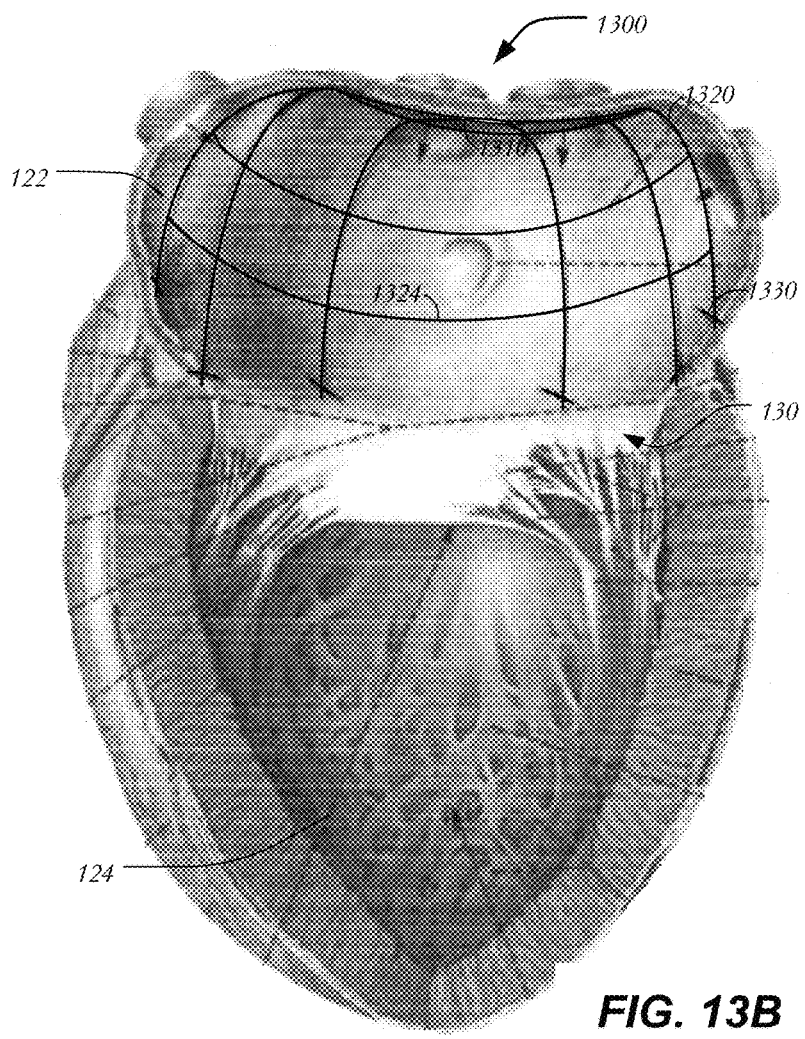

The use of tethering device 1300 to reshape mitral valve 130 is shown in FIG. 13B. As shown, hub 1310 is affixed to the tissue forming the upper wall of left atrium 122 using sutures, a biocompatible adhesive or other suitable arrangement. Cascading tethers 1320 extend from hub 1310 toward left ventricle 124 and couple to any of the aforementioned structures of the heart (e.g., an atrial wall, a fibrous ring, a papillary muscle, etc.) via anchors 1330. Adjustment of the functional lengths of tethers 1320 may be accomplished by pulling each tether through a one-way gate in an anchor as described above. With such adjustment, tethering device 1300 causes the shape of the mitral valve 130 to be remodeled to allow proper coaptation of the native valve leaflets. In a variant hereof, hub 1310 and lateral tethers 1324 may be eliminated, and cascading tethers 1320 may be coupled at their first ends 1321*a* directly to heart tissue (by suturing, anchors, and the like) at a common attachment point or at separate attachment points, and at their second ends 1321*b* (by anchors 1330) to different locations closer to the native valve being repaired.

Figure 14A:
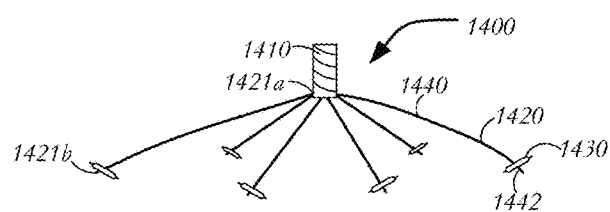
FIGS. 14A and 14B are, respectively, a side view of a fourth tethering device, and a schematic representation showing the use of the fourth tethering device on a native valve.

In yet another variation shown in FIG. 14A, a spider-like tethering device 1400 may be used to remodel heart tissue to aid leaflet coaptation. Tethering device 1400 includes adjusting member 1410 and a plurality of tethers 1420 joined at their first ends 1421*a* to adjusting member 1410 and extending to second or free ends 1421*b*. Six tethers 1420 are shown in the embodiment of FIG. 14A, although more or less tethers are possible as desired. In this example, each of the six tethers 1420 includes a functional portion 1440 and a terminal portion 1442, as well as an anchor 1430 adjacent its second end 1421*b*, the anchor including at least one piercing member. The length of the functional portion 1440 of each tether may be adjusted in any of the manners described above, i.e., by using a one-way gate.

Figure 14B:
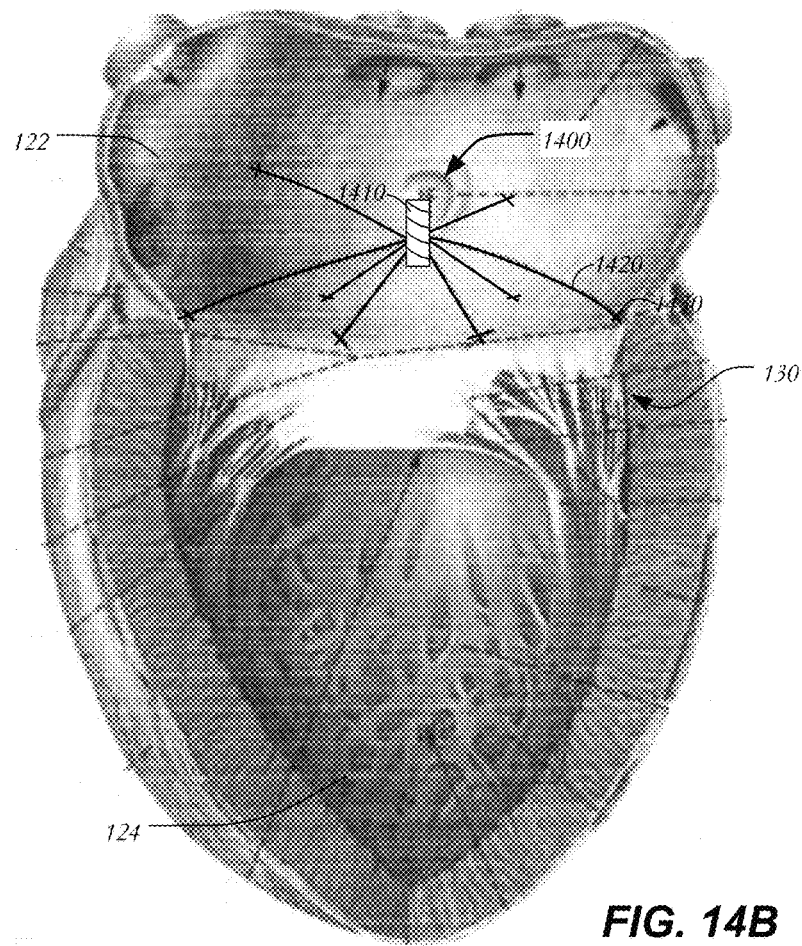

The use of tethering device 1400 to reshape mitral valve 130 is shown in FIG. 14B. Adjusting member 1410 may be affixed to the tissue forming left atrium 122 using sutures, a biocompatible adhesive or other suitable technique. Alternatively, adjusting member 1410 may be free-floating in left atrium 122 (e.g., adjusting member 1410 may be suspended in the left atrium between tethers 1420). Tethers 1420 extend from adjusting member 1410 toward opposing portions of left ventricle 124 and couple to any of the aforementioned structures of the heart via anchors 1430. In some examples suspension of adjusting member 1410 is possible because tethers 1420 pull the adjusting member in different or opposite directions. Adjustment of the functional lengths of tethers 1420 may be accomplished by rotating adjusting member 1410 to shorten all of the tethers or through adjustment at individual anchors as outlined above. In some examples, it is possible to include a two-part adjustment member 1410 such that rotating the upper portion with respect to the lower portion draws in all of the tethers 1420, effectively foreshortening all the tethers at once. As tethers 1420 pull various portions of the heart tissue toward adjusting member 1410, tethering device 1400 remodels the shape of mitral valve 130 to allow proper coaptation of the native valve leaflets.

According to the disclosure, one device for repairing a native heart valve may include a reinforcing structure configured to couple to a portion of the native heart valve to remodel the geometry of the native heart valve, and at least one supporting member extending from the reinforcing structure and in contact with heart tissue; and/or the reinforcing structure may include a collapsible and expandable toroidal body having a plurality of coils for fixing the toroidal body at a predetermined location in a native valve annulus and the at least one supporting member comprises a plurality of coils for connecting the toroidal body at a predetermined location in a native valve annulus; and/or the reinforcing structure may further include a plurality of hooks for coupling the toroidal body to at least a portion of the native heart valve; and/or the reinforcing structure may include a body having a shape corresponding to a perimeter of the native heart valve and at least one flap coupled to the body and configured to support at least one native leaflet of the native heart valve; and/or the reinforcing structure may include a rigid brace configured to couple to a fibrous ring of the native heart valve.

Another device for repairing a native heart valve may include a tethering structure including a plurality of tethers, each of the plurality of tethers extending between a first end and a second end, the second end having an anchor for coupling to a portion of heart tissue to remodel a geometry of a native heart valve; and/or the tethering structure further may include a base configured and arranged for coupling to a left atrial appendage, and the plurality tethers may be coupled to the base at first ends and to portions of heart tissue at second ends; and/or the device may further include an adjusting member coupled to the base and configured to collectively adjust the functional lengths of all of the plurality of tethers; and/or the tethering structure further may include a central hub coupled to the plurality of tethers, and the plurality of tethers may extend from the hub in multiple directions; and/or the tethering structure may be configured as a dome-like structure having an upper portion for coupling to a wall of a left atrium, and the plurality of tethers may include cascading tethers extending in a longitudinal direction from the upper portion; and/or the tethering structure further may include lateral tethers extending across the cascading tethers and coupled to the cascading tethers to form a net-like structure; and/or the tethering structure may include a free-floating spoke coupled to the plurality of tethers, and the plurality of tethers may be configured to couple to heart tissue such that the free-floating spoke is suspended in a left atrium; and/or the plurality of tethers may be configured to attach to at least one of an atrial wall, a ventricular wall, one or more of a native valve leaflet, a fibrous ring, a papillary muscle, chordae tendineae, a left atrial appendage, a vein or an artery.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for repairing a native heart valve, comprising:
an inflatable, collapsible and expandable, and continuously toroidal-shaped body having an inner perimeter and an outer perimeter, the inner perimeter defining an unobstructed opening and the outer perimeter being capable of matching a perimeter of the native heart valve, the body being configured to couple to at least a portion of the annulus of the native heart valve to remodel a geometry of the native heart valve;
a plurality of flexible coils extending from the body for coupling the body to the native heart valve; and
a plurality of hooks extending from an underside of the body for coupling the body to native valve leaflets.

2. The device of claim 1, wherein the body comprises a rigid brace configured to couple to a fibrous ring of the native heart valve.

3. The device of claim 1, wherein the body further includes an inflation port capable of receiving an inflation medium.

4. The device of claim 3, wherein the inflation medium is selected from one of saline, a gas, a polymeric material, a nitinol foam, or a gel.

5. The device of claim 1, wherein the inner perimeter and the outer perimeter are concentric.

6. The device of claim 1, wherein the plurality of flexible coils extend from the underside of the body.

* * * * *